(12) United States Patent
Hes et al.

(10) Patent No.: US 7,371,769 B2
(45) Date of Patent: May 13, 2008

(54) TETRAHYDROPYRIDIN-4-YL INDOLES WITH A COMBINATION OF AFFINITY FOR DOPAMINE-$D_2$ RECEPTORS AND SEROTONIN REUPTAKE SITES

(75) Inventors: Roelof van Hes, Weesp (NL); Pieter Smid, Weesp (NL); Cornelis G. Kruse, Weesp (NL); Martinus Th. M. Tulp, Weesp (NL)

(73) Assignee: Solvay Pharmaceuticals B.V., Weesp (NL)

( * ) Notice: Subject to any disclaimer, the term of this patent is extended or adjusted under 35 U.S.C. 154(b) by 49 days.

(21) Appl. No.: 11/294,657

(22) Filed: Dec. 6, 2005

(65) Prior Publication Data

US 2006/0122206 A1 Jun. 8, 2006
US 2007/0066634 A2 Mar. 22, 2007

Related U.S. Application Data

(60) Provisional application No. 60/633,439, filed on Dec. 7, 2004.

(51) Int. Cl.
*A01N 43/64* (2006.01)
*A61K 31/41* (2006.01)
*C07D 209/04* (2006.01)

(52) U.S. Cl. .......................... 514/359; 548/469; 546/1; 544/242

(58) Field of Classification Search ................ 514/359; 548/469; 546/1; 544/242
See application file for complete search history.

(56) References Cited

FOREIGN PATENT DOCUMENTS

| | | |
|---|---|---|
| DE | 487014 | 11/1929 |
| EP | 0 138 280 B1 | 4/1985 |
| EP | 0 189 612 B1 | 8/1986 |
| EP | 0 376 607 A1 | 7/1990 |
| EP | 0378 255 B1 | 7/1990 |
| EP | 0 900 792 | 3/1999 |
| GB | 1 378 080 | 12/1974 |
| WO | WO 97/36893 | 10/1997 |
| WO | WO 99/05140 | 2/1999 |
| WO | WO 99/51575 | 10/1999 |
| WO | WO 00/23441 | 4/2000 |
| WO | WO 00/43382 | 7/2000 |
| WO | WO 00/69424 A3 | 11/2000 |
| WO | WO 01/14330 A2 | 3/2001 |
| WO | WO 02/066473 A | 8/2002 |
| WO | WO 2004/020437 A1 | 3/2004 |
| WO | WO 2004/052886 A1 | 6/2004 |
| WO | WO 2004/054972 | 7/2004 |

OTHER PUBLICATIONS

Adcock, et al., "Fluorine-19 Substituent Chemical Shifts," Aust. J. Chem. vol. 23, pp. 1921-1937, (1970).

Badger, et al., "Thionaphthencarboxylic Acids," Journal of the Chemical Society, pp. 2624-2630, (1957).

Beattie, et al., "The Synthesis of Nine Chloroidonaphthalenes," Journal of The Chemical Society, pp. 50-52, (1934).

Berg, et al., "The Search for Chemotherapeutic Amidines. Part X Substituted 4:4'-Diamidino-αω-diphenoxyalkanes and -diphenyl Ethers," Journal of The Chemical Society, pp. 642-648, (1949).

Bickel, "The Pharmacology and Biochemistry of N-Oxides," Pharmacological Reviews, 21(4), pp. 325-355, (1969).

Buchan, et. al., "The Chlorination of Iodophenols. The Chlorination of o-Iodophenol," Journal of The Chemical Society, pp. 137-145, (1931).

(Continued)

*Primary Examiner*—James O. Wilson
*Assistant Examiner*—Paul V. Ward
(74) *Attorney, Agent, or Firm*—Finnegan, Henderson, Farabow, Garrett & Dunner

(57) ABSTRACT

The present invention relates to a group of novel tetrahydropyridin-4-yl indoles with a dual mode of action: serotonin reuptake inhibition and affinity for dopamine-$D_2$ receptors, to methods for the preparation of these compounds and to novel intermediates useful for the synthesis of said tetrahydropyridin-4-yl indoles. The invention also relates to the use of a compound disclosed herein for the manufacture of a medicament giving a beneficial effect.

The invention relates to novel tetrahydropyridin-4-yl indoles of the formula.

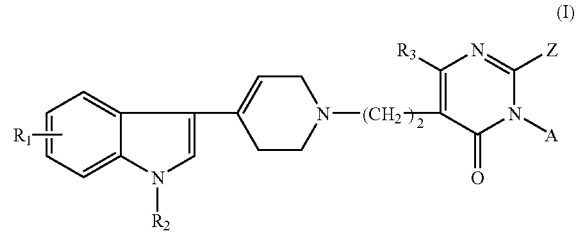

(I)

and tautomers, stereoisomers, prodrugs, N-oxides, pharmacologically acceptable salts, hydrates and solvates thereof, wherein:

$R_1$ is hydrogen, halogen, alkyl($C_{1-3}$) or alkoxy($C_{1-3}$), CN or $CF_3$, $R_2$ is hydrogen or alkyl($C_{1-3}$), $R_3$ is hydrogen or alkyl($C_{1-3}$), Z is hydrogen or alkyl($C_{1-3}$), alkoxy($C_{1-3}$) or alkylthio ($C_{1-3}$), A is hydrogen or alkyl($C_{1-3}$), or A and Z together form a saturated or (partly) unsaturated 5- or 6-membered ring which may be substituted with halogen, alkyl ($C_{1-3}$) or phenyl, in which ring Z represents carbon, sulfur of nitrogen.

18 Claims, No Drawings

OTHER PUBLICATIONS

Campos et al., "A General Synthesis of Substituted Indoles from Cyclic Enol Ethers and Enol Lactones," Organic Letters, vol. 6, No. 1, pp. 79-82, (2004).

Costall et al., "Climbing Behavior Induced by Apormorphine in Mice: A Potential Model for the Detection of Neurolaptic Activity," Eur. J. Pharmacol., vol. 1, pp. 39-50 (1978).

Davison et al., "Nitrone dipolar Cycloaddition routes to piperidines and indolizidines, Part 9. Formal synthesis of (−)-pinidine and total synthesis of (−)-histrionicotoxin, (+)-histrionicotoxin and (−)-histrioncotoxin 235A," J. Chem. Soc., Perkins Trans. 1, pp. 1494-1514, (2002).

Feenstra et al. "Antiparkinsonian Antidepressant Anxiolytic Dopamine $D_2$ Partial Agonist 5-HT $1_a$ Agonist," Drugs of the Future, vol. 26, No. 2, pp. 128-132, (2001).

Feenstra et al., "New 1-aryl-4-(biarylmethylene)piperazines as potential atypical antipsychotics sharing dopamine D2 receptor and serotonin 5HT1A receptor affinities," Bioorg. & Med. Chem. Lett., 11, pp. 2345-2349 (2001).

Finger et al., "Aromatic Fluorine Compounds. VIII. Plant Growth Regulators and Intermediates," pp. 94-101 , (1959).

Huang et al., "Expanding Pd-Catalyzed C-N Bond-Forming Processes: The First Amidation of Aryl Sulfonates, Aqueous Amination, and Complementarity with Cu-Catalyzed Reactions," J. AM. Chem. Soc., vol. 125, No. 22, pp. 6653-6655, 2003.

Jacobs, B.L., "An Animal Behaviour Model for Studying Central Seratongergic. Synapses," Life Sci., vol. 19, No. 6, pp. 777-785 (1976).

Leclerc, et al., "5-Halobenzothiophene Analogues of Melatonin: Synthesis and Affinity for mt1 and MT2 Receptors in Man," Pharm. Pharmacol. Commun., pp. 61-65, (2000).

Mancuso, et al., "Activated Dimethyl Sulfoxide: Useful Reagents for Synthesis," Int'l. Journal of Methods in Synthetic Organic Chemistry, pp. 165-248, (1981).

Ruchardt et al., "Durchfuhrung der Jacobsonschen Indazolsynthese im Eintopfverfahren," Liebigs Ann. Chem, pp. 908-927, (1980).

Samuel Weiss et al., "Corticotropin-Peptide Regulation of Intracellular Cyclic AMP Production in Cortical Neurons in Primary Culture," Journal of Neurochemistry, vol. 45, No. 3, pp. 869-874, (1985).

Searles, "The Reaction of Trimethylene Oxide with Grignard Reagents and Organolithium Compounds," Trimethylene Oxide with Grignard and Organolithium Reagents, p. 124-125, (1951).

Timms et al., "Bioorganic and Medicinal Chemistry Letters," vol. 14, No. 10, pp. 2469-2472, (2004).

Van Hes et al, Bioorganic and Medicinal Chemistry Letters, vol. 13, No. 3, pp. 405-408, (2003).

Yoram Solomon, et al., "A Highly Sensitive Adenylate Cyclase Assay," Analytical Biochemistry 58, pp. 541-548, (1974).

Yu, et al., "20-Hydroxyeicosatetraenoic Acid (20-HETE): Structural Determinants for Renal Vasoconstriction," Bioorg. Med. Chem. 11, pp. 2803-2821, (2003).

Creese, et al., "[$^3$H]-Spiroperidol Labels Dopamine Receptors in Pituitary and Brain," Eur. J. Pharmacol., vol. 46., pp. 377-381, (1977).

Habert, et al., "Characterisation of [$^3$H]-paroxetine Binding to Rat Cortical Membranes," Eur. J. Pharmacol., vol. 118, pp. 107-114, (1985).

Stella, "Prodrugs as Therapeutics," Expert Opin. Ther. Patents, vol. 14, No. 3, pp. 277-280, (2004).

King, "Bioisosteres, Conformational Restriction, and Prodrugs—Case History: An Example of a Conformational Restriction Approach," Medicinal Chemistry: Principles and Practice, pp. 206-225, (ISBN 0-85186-494-5), (1994).

Organic Process Research and Development, vol. 1, No. 4, pp. 300-310, (1997).

Ettmayer, et al., "Lessons Learned from Marketed and Investigational Prodrugs," J. Med. Chem., 47, pp. 2393-2404, (2004).

Van Der Heyden, et al., "A Rapidly Acquired One-Way Conditioned Avoidance Procedure in Rats as a Primary Screening Test for Antipsychotics: Influence of Shock Intensity on Avoidance Performance", Behavioural Brain Research, vol. 31, pp. 61-67, (1988).

Van Der Poel, et al., "Temporal Patterning of Ultrasonic Distress Calls in the Adult Rat: Effects of Morphine and Benzodiazepines", Psycho-pharmacology, vol. 97, pp. 147-148, (1989).

Boschman, et al., "Invitro Inhibition of ADP-induced platelet Aggregation by O- (aminoalkyl) oxime ethers," European J. of Medicinal Chem., vol. 15, No. 4, pp. 351-356 (Jul. 1980).

Tims, et al. "SAR Development of a Selective 5-HT1D Antagonist/ Serotonin Reuptake Inhibitor Lead Using Rapid Parallel Synthesis," Bioorg. Med. Chem. vol. 14, No. 10, pp. 2469-2472, (2004).

Van Hes, et al., "SLV310, A Novel, Potential Antipsychotic, Combining Potent Dopamine D2 Receptor Antagonism with Serotonin Reuptake Inhibition," Biorg. Med. Chem., vol. 13, No. 3, pp. 405-408, (2003).

TETRAHYDROPYRIDIN-4-YL INDOLES WITH A COMBINATION OF AFFINITY FOR DOPAMINE-$D_2$ RECEPTORS AND SEROTONIN REUPTAKE SITES

This application claims the benefit of U.S. Provisional Application No. 60/633,439, filed Dec. 7, 2004, the content of which is incorporated herein by reference.

The present invention relates to a group of novel tetrahydropyridin-4-yl indoles with a dual mode of action: serotonin reuptake inhibition and affinity for dopamine-$D_2$ receptors, to methods for the preparation of these compounds and to novel intermediates useful for the synthesis of said tetrahydropyridin-4-yl indoles. The invention also relates to the use of a compound disclosed herein for the manufacture of a medicament giving a beneficial effect. A beneficial effect is disclosed herein or apparent to a person skilled in the art from the specification and general knowledge in the art. The invention also relates to the use of a compound of the invention for the manufacture of a medicament for treating or preventing a disease or condition. More particularly, the invention relates to a new use for the treatment of a disease or condition disclosed herein or apparent to a person skilled in the art from the specification and general knowledge in the art. In embodiments of the invention specific compounds disclosed herein are used for the manufacture of a medicament useful in the treatment of disorders in which dopamine-$D_2$ receptors and serotonin reuptake sites are involved, or that can be treated via manipulation of those targets.

Tetrahydropyridin-4-yl indole derivatives with a dual action as dopamine-$D_2$ antagonists and serotonin reuptake inhibitors are known from WO 00/023441 and WO 00/069424, and a promising clinical candidate disclosed in these patent applications was further described by Van Hes et al. (Bioorganic and Medicinal Chemistry Letters, 13(3), 405-408, 2003). In a publication by Timms et al., (Bioorganic and Medicinal Chemistry Letters, 14(10), 2469-2472, 2004) tetrahydropyridin-4-yl indole derivatives with a dual action as serotonin 5-$HT_{1D}$ antagonists and serotonin reuptake inhibitors are described, and also in this group of compounds some were shown to possess dopamine-$D_2$ antagonistic activity. In WO 2004/020437 one specific compound is described as dopamine-$D_4$ antagonist and serotonin reuptake inhibitor: S-(+)-3-{1-[2-(2,3-dihydro-1 H-indol-3-yl)ethyl]-3,6dihydro-2H-pyridin-4-yl}-6-chloro-1H-indole. Of this compound no dopamine-$D_2$ affinity c.q. activity was disclosed.

The goal of the present invention was to provide further compounds with a dual action as dopamine-$D_2$ antagonists and serotonin reuptake inhibitors.

Surprisingly, potent dopamine-$D_2$ antagonistic activity combined with potent serotonin reuptake inhibitory activity was found in a group of novel 1,2,3,6-tetrahydropyridin-4-yl indoles of the formula (I)

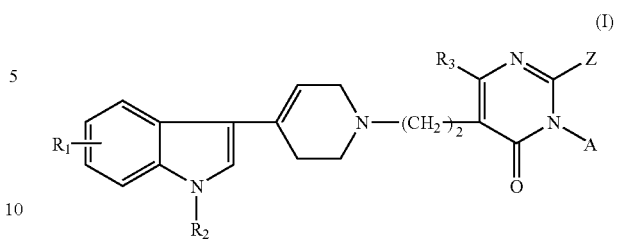

and tautomers, stereoisomers, prodrugs, N-oxides, pharmacologically acceptable salts, hydrates and solvates thereof, wherein:
$R_1$ is hydrogen, halogen, alkyl($C_{1-3}$) or alkoxy($C_{1-3}$), CN or $CF_3$,
$R_2$ is hydrogen or alkyl($C_{1-3}$),
$R_3$ is hydrogen or alkyl($C_{1-3}$),
Z is hydrogen or alkyl($C_{1-3}$), alkoxy($C_{1-3}$) or alkylthio ($C_{1-3}$),
A is hydrogen or alkyl($C_{1-3}$), or
A and Z together form a saturated or (partly) unsaturated 5- or 6-membered ring which may be substituted with halogen, alkyl ($C_{1-3}$) or phenyl, in which ring Z represents carbon, sulfur of nitrogen.

In the description of the substituents the abbreviation alkyl($C_{1-3}$) means methyl, ethyl, n-propyl or isopropyl.

Prodrugs of the compounds mentioned above are in the scope of the present invention. Prodrugs are therapeutic agents which are inactive per se but are transformed into one or more active metabolites. Prodrugs are bioreversible derivatives of drug molecules used to overcome some barriers to the utility of the parent drug molecule. These barriers include, but are not limited to, solubility, permeability, stability, presystemic metabolism and targeting limitations (Medicinal Chemistry: Principles and Practice, 1994, ISBN 0-85186-494-5, Ed.: F. D. King, p. 215; J. Stella, "*Prodrugs as therapeutics*", Expert Opin. Ther. Patents, 14(3), 277-280, 2004; P. Ettmayer et al., "*Lessons learned from marketed and investigational prodrugs*", J. Med. Chem., 47, 2393-2404, 2004). Pro-drugs, i.e. compounds which when administered to humans by any known route, are metabolised to compounds having formula (1), belong to the invention. In particular this relates to compounds with primary or secondary amino or hydroxy groups. Such compounds can be reacted with organic acids to yield compounds having formula (1) wherein an additional group is present which is easily removed after administration, for instance, but not limited to amidine, enamine, a Mannich base, a hydroxyl-methylene derivative, an O-(acyloxymethylene carbamate) derivative, carbamate, ester, amide or enaminone.

N-oxides of the compounds mentioned above are in the scope of the present invention. Tertiary amines may or may not give rise to N-oxide metabolites. The extend to what N-oxidation takes place varies from trace amounts to a near quantitative conversion. N-oxides may be more active than their corresponding tertiary amines or less active. Whilst N-oxides are easily reduced to their corresponding tertiary amines by chemical means, in the human body this happens to varying degrees. Some N-oxides undergo nearly quantitative reductive conversion to the corresponding tertiary amines, in other cases the conversion is a mere trace reaction or even completely absent. (M. H. Bickel: "*The pharmacology and Biochemistry of N-oxides*", Pharmacological Reviews, 21(4), 325-355, 1969).

Preferred compounds of the invention are compounds having formula (I) wherein $R_1$ is hydrogen or halogen, $R_2$ is hydrogen, $R_3$ is $CH_3$, Z is $SCH_3$ and A is $CH_3$, or Z+A from a (partly) unsaturated 6-membered ring which may be substituted with $CH_3$, $C_2H_5$ or i-$C_3H_7$.

Especially preferred is the compounds having formula (I) wherein $R_1=R_2=H$, $R_3$ is $CH_3$ and Z+A together represent $C(CH_3)=CH-CH=CH-$, and the salts thereof.

It has been found that the compounds according to the invention show high affinity for both the dopamine $D_2$ receptor and the serotonin reuptake site. This combination is useful for the treatment of schizophrenia and other psychotic disorders which enables a more complete treatment of all disease symptoms (e.g. positive symptoms and negative symptoms).

Some of the compounds having formula (I) show partial agonist activity at dopamine receptors making them particularly suitable for the treatment of Parkinson's disease.

The compounds show activity as antagonists at dopamine $D_2$ receptors as they potentially antagonize apomorphine-induced climbing behaviour in mice. The compounds also show activity as inhibitors of serotonin reuptake, as they potentiate 5-HTP induced behaviour in mice.

The compounds are active in therapeutic models sensitive to clinically relevant antipsychotics (e.g. the conditioned avoidance response; Van der Heyden & Bradford, Behav. Brain Res., 1988, 31:61-67) and antidepressants or anxiolytics (e.g. suppression of stress-induced vocalization; van der Poel et al., Psycho-pharmacology, 1989, 97: 147-148).

In contrast to clinically relevant dopamine $D_2$ receptor antagonists the described compounds have a low propensity to induce catalepsy in rodents and as such are likely to induce less extrapyramidal side effects than existing antipsychotic agents.

The inhibitory activity of serotonin reuptake inherent in these compounds may be responsible for the therapeutic effects observed in behavioural models sensitive to either antidepressants or anxiolytics.

The compounds can be used for the treatment of affections or diseases of the central nervous system caused by disturbances in either the dopaminergic or serotonergic systems, for example: aggression, anxiety disorders, autism, vertigo, depression, disturbances of cognition or memory, Parkinson's disease, and in particular schizophrenia and other psychotic disorders.

General Aspects of Syntheses

The compounds having formula (I) can be prepared by reaction of a compound of the formula

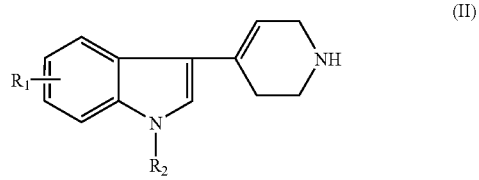

(II)

with a compound of the formula

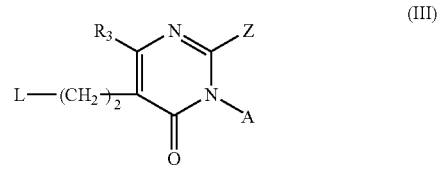

(III)

wherein the symbols $R_1$, $R_2$, $R_3$, Z and A have the above meanings, and L is a so-called leaving group, for example halogen or mesyl group.

This reaction is preferably carried out in an organic solvent such as acetonitrile in the precence of triethylamine or $K_2CO_3$ and KI at reflux temperature.

The starting compounds for this synthesis of the formula (II) can be obtained in a manner known per se by reacting an optionally substituted indole derivative with 4-piperidone.

The staring compounds having formula (III) can be obtained according to methods known for the synthesis of analogous compounds.

The selection of the particular synthetic procedures depends on factors known to those skilled in the art such as the compatibility of functional groups with the reagents used, the possibility to use protecting groups, catalysts, activating and coupling reagents and the ultimate structural features present in the final compound being prepared.

Pharmaceutically acceptable salts may be obtained using standard procedures well known in the art, for example by mixing a compound of the present invention with a suitable acid, for instance an inorganic acid such as hydrochloric acid, or with an organic acid.

Pharmaceutical Preparations

The compounds of the invention can be brought into forms suitable for administration by means of usual processes using auxiliary substances such as liquid or solid carrier material. The pharmaceutical compositions of the invention may be administered enterally, orally, parenterally (intramuscularly or intravenously), rectally or locally (topically). They can be administered in the form of solutions, powders, tablets, capsules (including microcapsules), ointments (creams or gel) or suppositories. Suitable excipients for such formulations are the pharmaceutically customary liquid or solid fillers and extenders, solvents, emulsifiers, lubricants, flavorings, colorings and/or buffer substances. Frequently used auxiliary substances which may be mentioned are magnesium carbonate, titanium dioxide, lactose, mannitol and other sugars, talc, lactoprotein, gelatin, starch, cellulose and its derivatives, animal and vegetable oils such as fish liver oil, sunflower, groundnut or sesame oil, polyethylene glycol and solvents such as, for example, sterile water and mono- or polyhydric alcohols such as glycerol.

Compounds of the present invention are generally administered as pharmaceutical compositions which are important and novel embodiments of the invention because of the presence of the compounds, more particularly specific compounds disclosed herein. Types of pharmaceutical compositions that may be used include but are not limited to tablets, chewable tablets, capsules, solutions, parenteral solutions, suppositories, suspensions, and other types disclosed herein or apparent to a person skilled in the art from the specification and general knowledge in the art. In embodiments of the invention, a pharmaceutical pack or kit is provided comprising one or more containers filled with one or more of the ingredients of a pharmaceutical composition of the invention. Associated with such container(s) can be various written materials such as instructions for use, or a notice in the form prescribed by a governmental agency regulating the manufacture, use or sale of pharmaceuticals products, which notice reflects approval by the agency of manufacture, use, or sale for human or veterinary administration.

Pharmacological Methods

In vitro Affinity for Dopamine-$D_2$ Receptors

Affinity of the compounds for dopamine-$D_2$ receptors was determined using the receptor binding assay described by I. Creese, R. Schneider and S. H. Snyder: "[$^3$H]-Spiroperidol labels dopamine receptors in rat pituitary and brain", Eur. J. Pharmacol., 46, 377-381,1977.

In vitro Affinity for Serotonin Reuptake Sites

Affinity of the compounds for serotonin reuptake sites was determined using the receptor binding assay described by E. Habert et al.,: "Characterisation of [$^3$H]-paroxetine binding to rat cortical membranes", Eur. J. Pharmacol., 118, 107-114, 1985.

Dosages

The affinity of the compounds of the invention for dopamine-$D_2$ receptors and serotonine reuptake sites was determined as described above. From the binding affinity measured for a given compound of formula (1), one can estimate a theoretical lowest effective dose. At a concentration of the compound equal to twice the measured $K_i$-value, 100% of the receptors likely will be occupied by the compound. Converting that concentration to mg of compound per kg of patient yields a theoretical lowest effective dose, assuming ideal bioavailability. Pharmacokinetic, pharmacodynamic, and other considerations may alter the dose actually administered to a higher or lower value. The dosage expediently administered is 0.001-1000 mg/kg, preferably 0.1-100 mg/kg of patient's bodyweight.

Treatment

The term "treatment" as used herein refers to any treatment of a mammalian, preferably human condition or disease, and includes: (1) preventing the disease or condition from occurring in a subject which may be predisposed to the disease but has not yet been diagnosed as having it, (2) inhibiting the disease or condition, i.e., arresting its development, (3) relieving the disease or condition, i.e., causing regression of the condition, or (4) relieving the conditions caused by the disease, i.e., stopping the symptoms of the disease.

The preparation of the compounds having formula (I) will now be described in more detail in the following Examples.

EXAMPLES

Example 1

Materials and Methods $^1$H and $^{13}$C NMR spectra were recorded on a Bruker Avance DRX600 instrument (600 MHz), Varian UN400 instrument (400 MHz) or on a Varian VXR200 instrument (200 MHz) using DMSO-$D_6$ or $CDCl_3$ as solvents with tetramethylsilane as an internal standard. Chemical shifts are given in ppm (5 scale) downfield from tetramethylsilane. Coupling constants (J) are expressed in Hz. Flash chromatography was performed using silica gel 60 (0.040-0.063 mm, Merck). Column chromatography was performed using silica gel 60 (0.063-0.200 mm, Merck). Melting points were recorded on a Büchi B-545 melting point apparatus.

Mass spectra were recorded on a Micromass QTOF-2 instrument with MassLynx application software for acquisition and reconstruction of the data. Exact mass measurement was done of the quasimolecular ion [M+H]$^+$.

Example 2

Syntheses of Specific Compounds

Compound No. 26 a) Preparation of 5-fluoro-3-(1,2,3,6, -tetrahydropyridin-4-yl)indole.

To a solution of sodium (60 g, 2.6 mol) in 1000 ml of methanol was added 5-fluoroindole (49 g, 0.36 mol) and 4-piperidone.$H_2O$.HCl (170 g, 1.11 mol). The mixture was heated under reflux for 18 h, then concentrated, water was added and extracted with ethyl acetate. The combined organic layer was dried over sodium sulfate and then concentrated. The resulting solid was dissolved in methanol (about 200 ml) and then diluted with water (about 1000-1500 ml). The precipitate was collected, washed with water and petroleum ether and then dried in a vacuum oven at 60° C. Yield 74 g (95%) of a yellow solid.

b) Preparation of 3-(2-chloroethyl)-2,9-dimethyl-4H-pyrido[1,2-a]-pyrimidin-4-one.

To a solution of 2-amino-3-picoline (3.3 9, 30 mmol) in phosphorus oxychloride (11 ml) was added 2-acetylbutyrolactone (3.25 ml, 30 mmol). The mixture was heated at 100° C. for 18 hours, cooled, poured on ice, made basic with a 2N sodium hydroxide solution and extracted with ethyl acetate. The organic layer was separated, dried, concentrated and purified by silica gel column chromatography (dichloromethane/methanol=95/5). Yield 2.5 g (35%) of white solid.

c) Preparation of 3-[2-[4-(5-fluoro-1H-indol-3-yl)-1,2,3,6-tetrahydro-pyridin-1-yl]ethyl]-2,9-dimethyl-4H-pyrido[1,2-a]pyrimidin-4-one.

A solution of 5-fluoro-3-(1,2,3,6-tetrahydropyridin-4-yl)indole (5.5 g, 0.025 mol), 3-(2-chloroethyl)-2,9-dimethyl-4H-pyrido[1,2-a]pyrimidin-4-one (7.2 g, 0.030 mol), diisopropylamine (5 ml) and potassium iodide (1 g) in acetonitrile (100 ml) was heated under reflux for 24 h. After cooling the precipitate was collected and washed with acetonitrile (20 ml), isopropyl alcohol (3×20 ml) and petroleum ether (25 ml) respectively. Yield 7.13 g (67%) of a pale yellow solid. M.p.: 229-230° C.

Free Base of Compound No.22 a) Preparation of 3-(1,2,3,6-tetrahydropyridin-4-yl)indole.

To a solution of sodium methoxide (450 ml, 30% in methanol, 2.5 mol) in 1000 ml of methanol was added indole (50 g, 0.427 mol) and 4-piperidone.H$_2$O.HCl (162 g, 1.05 mol). The mixture was heated under reflux for 18 h forming a yellow precipitate. The mixture was concentrated and water (1000 ml) was added. The precipitate was collected, washed with water and petroleum ether and then dried in a vacuum oven at 50° C. Yield 77 g (91%) of a pale yellow solid.

b) Preparation of 3-[2-[4-(1H-indol-3-yl)-1,2,3,6-tetrahydropyridin-1-yl]-ethyl]-2,9-dimethyl-4H-pyrido[1,2-a]pyrimidin-4-one.

A solution of 3-(1,2,3,6-tetrahydropyridin-4-yl)indole (25 g, 0.126 mol), 3-(2-chloroethyl)-2,9-dimethyl-4H-pyrido[1,2-a]pyrimidin-4-one (33 g, 0.139 mol) and potassium carbonate (17.5 g, 0.127 mol) in acetonitrile (500 ml) and water (100 ml) was heated under reflux for 18 h. After cooling the precipitate was collected and washed with water, isopropyl alcohol and petroleum ether respectively. Yield 38 g (76%) of a pale yellow solid. M.p.: 210-212° C.

Compound No. 12 a) Preparation of 2-thio-5-(2-hydroxyethyl)-6-methyluracil.

To a solution of sodium (55.6 g, 2.4 mol) in ethanol (1000 ml) was added slowly 2-acetylbutyrolactone 155 g, 1.2 mol) after which thiourea (128 g, 1.65 mol) was added in small portions. The mixture was heated under reflux for 16 h, then concentrated, water (800 ml) was added and acidified slowly with concentrated hydrochloric acid (200 ml). The precipitate was collected and washed with water, isopropyl alcohol and petroleum ether. Yield 125 g (56%) of a white solid.

b) Preparation of 2-methylthio-5-(2-hydroxyethyl)-6-methyl-3H-pyrimidin-4-one.

To a suspension of 2-thio-5-(2-hydroxyethyl)-6-methyluracil (50 g, 0.26 mol) in DMF (320 ml) was added slowly one equivalent of sodium hydride. Next was added slowly one equivalent of methyl iodide (16.6 ml). The mixture was stirred for two hours at 30° C., after which water (800 ml) was added. The precipitate was collected and washed with water, isopropyl alcohol and petroleum ether. Yield 34.4 g (64%).

c) Preparation of 2-methylthio-5-(2-hydroxyethyl)-3,6-dimethyl-3H-pyrimidin-4-one To a suspension of 2-methylthio-5-(2-hydroxyethyl)-6-methyl-3H-pyrimidin-4-one (34 g, 0.17 mol) in DMF (300 ml) was added slowly one equivalent of sodium hydride (55%, 7.4 g). Next was added slowly one equivalent of methyl iodide (10.5 ml). The mixture was stirred for two hours at 50° C., after which most of the DMF was removed in vaccuum. Water was added and the mixture was extracted with ethyl acetate. The combined organic layer was dried over sodium sulfate and then concentrated and purified by flash chromatografy (eluens: ether followed by ether/methanol=9/1). Yield 20.3 g (56%), mp. 117-118° C.

d) Preparation of 2-methylthio-5-(2-chloroethyl)-3,6-dimethyl-3H-pyrimidin-4-one.

To a solution of 2-methylthio-5-(2-hydroxyethyl)-3,6-dimethyl-3H-pyrimidin-4-one (20.3 g, 0.095 mol) in chloroform (200 ml) was added one equivalent of pyridine (7.6 ml), followed by slow addition of three equivalents of thionyl chloride (21 ml). After stirring for 15 minutes, the mixture was concentrated and water (300 ml) was added. The precipitate was collected and washed with water, isopropyl alcohol and petroleum ether. Yield 34.4 g (64%). Yield 20.3 g (92%). Mp. 135-137° C.

e) Preparation of 5-[2-[4-(1H-indol-3-yl)-1,2,3,6-tetrahydropyridin-1-yl]ethyl]-2-methylthio-3,6-dimethyl-3H-pyrimidin-4-one.

To a solution of 3-(1,2,3,6-tetrahydropyridin-4-yl)indole (1.0 g, 5 mmol) in acetonitrile (30 ml) was added 2-methylthio-5-(2-chloroethyl)-3,6-dimethyl-3H-pyrimidin-4-one (1.42 g, 6.1 mmol), potassium iodide (0.84 g, 5 mmol) and triethylamine (1.4 ml, 10 mmol). The mixture was heated at 80° C. for 8 hours, cooled, concentrated and purified by flash chromatografy (dichloromethane/methanol/ammonia=95/4.5/0.5)

Yield: 1.83 g (92%) of a yellow compound. Mp. 245-246° C.

Compound No. 18 a) Preparation of 2-methoxy-5-(2-hydroxyethyl)-6-methyl-3H-pyrimidin-4-one.

To a solution of O-methylisourea hydrogen sulfate (17.2 g, 0.1 mol) in water (90 ml) was added calcium hydroxide (8.14 g, 0.11 mol) followed by a solution of 2-acetylbutyrolactone (10.7 ml, 0.1 mol) in ethanol (70 ml). The mixture was stirred at room temperature for two days, filtered and washed with ethanol. The filtrate was concentrated in vaccuum and purified by flash chromatografy (dichloromethane/methanol=95/5). Yield 2.6 g (14%) of a white solid.

b) Preparation of 2-methoxy-5-(2-hydroxyethyl)-3,6-dimethyl-3H-pyrimidin-4-one.

To a suspension of 2-methoxy-5-(2-hydroxyethyl)-6-methyl-3H-pyrimidin-4-one (2.6 g, 0.014 mol) in DMF (25 ml) was added one equivalent of sodium hydride (55%, 0.6 g). After stirring for 0.5 hr. methyl iodide (0.81 ml, 0.014 mol) was added and the mixture was heated at 50° C. for five hours. After cooling, most of the DMF was removed in vaccuum. Water was added and the mixture was extracted with ethyl acetate. The combined organic layer was dried over sodium sulfate and then concentrated. Yield 2.0 g (71%) of a yellow oil.

c) Preparation of 2-methoxy-5-(2-mesyloxyethyl)-3,6-dimethyl-3H-pyrimidin-4-one.

To a solution of 2-methoxy-5-(2-hydroxyethyl)-3, 6-dimethyl-3H-pyrimidin-4-one (2.0 g, 0.01 mol) in dry ethyl acetate (100 ml) was added triethylamine (2.7 ml). After cooling in icewater, mesylchloride (0.9 ml, 0.011 mol) was added slowly. After stirring for 16 hours at room temperature the precipitate was filtered off and the filtrate (70 ml) was used without further purification.

d) Preparation of 5-[2-[4-(1H-indol-3-yl)-1,2,3,6-tetrahydropyridin-1-yl]ethyl]-2-methoxy-3,6-dimethyl-3H-pyrimidin-4-one.

To the above mentioned filtrate (35 ml, about 5 mmol) was added 3-(1,2,3,6-tetrahydropyridin-4-yl)indole (1.0 g, 5 mmol), triethylamine (2 ml), potassium iodide (0.84 g, 5 mmol) and acetonitrile (50 ml). The mixture was heated at 80° C. for 16 hours and then concentrated and purified by flash chromatografy (eluens: dichloromethane/methanol/ammonia=95/4.5/0.5). Yield 0.5 g (26%), mp. 209-211° C.

The compounds with formula (I) listed in the table below have been prepared according to the methods of Examples 1 to 4.

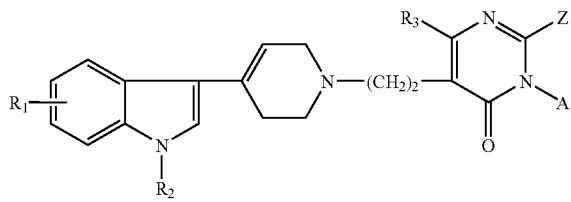

| No | R₁ | R₂ | R₃ | Z | A | (Z + A) Z A | Salt or free base | Melting point (° C.) |
|---|---|---|---|---|---|---|---|---|
| 1 | H | H | CH₃ | — | — | —CH=CH—CH=CH— | HCl | 205 (dec.) |
| 2 | 7-Cl | H | CH₃ | — | — | —CH=CH—CH=CH— | fb | 232-3 |
| 3 | 5-CH₃ | H | CH₃ | — | — | —CH=CH—CH=CH— | fb | 206-7 |
| 4 | 6-Cl | H | CH₃ | — | — | —CH=CH—CH=CH— | fb | 246-8 |
| 5 | 5-Cl | H | CH₃ | — | — | —CH=CH—CH=CH— | fb | amorph |
| 6 | 5-CN | H | CH₃ | — | — | —CH=CH—CH=CH— | fb | amorph |
| 7 | 5-F | H | CH₃ | — | — | —CH=CH—CH=CH— | fb | 226-7 (d.) |
| 8 | 5-Br | H | CH₃ | — | — | —CH=CH—CH=CH— | HCl | amorph |
| 9 | H | H | CH₃ | — | — | —CH=CH—C(CH₃)=CH— | HCl | amorph |
| 10 | H | H | CH₃ | — | — | —S—CH₂—CH₂— | HCl | amorph |
| 11 | H | H | CH₃ | — | — | —S—CH=CH— | HCl | amorph |
| 12 | H | H | CH₃ | SCH₃ | CH₃ | — | fb | 245-6 |
| 13 | 7-CH₃ | H | CH₃ | — | — | —CH=CH—CH=CH— | fb | 226-7 |
| 14 | H | H | CH₃ | SCH₃ | H | — | fb | amorph |
| 15 | H | H | CH₃ | — | — | —CH=C(CH₃)—CH=CH— | HCl | 261-4 |
| 16 | H | H | CH₃ | — | — | —S—CH=C(C₆H₅)— | fb | 220-3 |
| 17 | H | H | CH₃ | — | — | —NH—(CH₂)₃— | fb | 249-52 |
| 18 | H | H | CH₃ | OCH₃ | CH₃ | — | HCl | 209-11 |
| 19 | 5-F | H | CH₃ | SCH₃ | CH₃ | — | fb | 229 (dec.) |
| 20 | H | CH₃ | CH₃ | SCH₃ | CH₃ | — | HCl | amorph |
| 21 | 5-F | H | CH₃ | — | — | —CH=C(CH₃)—CH=CH— | fb | glass |
| 22 | H | H | CH₃ | — | — | —C(CH₃)=CH—CH=CH— | CH₃SO₃H | 242-6 |
| 23 | H | H | CH₃ | — | — | —CH=CH—CH=C(CH₃)— | fb | 207-9 |
| 24 | 5-F | H | CH₃ | — | — | —CH=C(C₂H₅)—CH=CH— | fb | 198-201 |
| 25 | H | H | CH₃ | — | — | —CH=C(C₂H₅)—CH=CH— | fb | 203-7 |
| 26 | 5-F | H | CH₃ | — | — | —C(CH₃)=CH—CH=CH— | fb | 229-30 |
| 27 | H | H | CH₃ | — | — | —CH=C(C₆H₅)—CH=CH— | fb | 211-24 |
| 28 | 5-F | H | CH₃ | — | — | —CH=C(i-C₃H₇)—CH=CH— | fb | amorph |
| 29 | H | H | CH₃ | — | — | —CH=C(i-C₃H₇)—CH=CH— | fb | 202-4 |
| 30 | 5-Cl | H | C₂H₅ | H | CH₃ | — | fb | 204-7 |
| 31 | 5-Br | H | C₂H₅ | H | CH₃ | — | fb | 205-8 |
| 32 | 5-CN | H | C₂H₅ | H | CH₃ | — | fb | 227-30 |
| 33 | 5-F | H | CH₃ | H | CH₃ | — | fb | 234-5 (d.) |

Example 3

Formulation of Compound 22 in Animal Studies

For oral (p.o.) administration: to the desired quantity (0.5-5 mg) of the solid compound 22 in a glass tube, some glass beads were added and the solid was milled by vortexing for 2 minutes. After addition of 1 ml of a solution of 1% methylcellulose in water and 2% (v/v) of Poloxamer 188 (Lutrol F68), the compound was suspended by vortexing for 10 minutes. The pH was adjusted to 7 with a few drops of aqueous NaOH (0.1 N). Remaining particles in the suspension were further suspended by using an ultrasonic bath.

For intraperitoneal (i.p.) administration: to the desired quantity (0.5-15 mg) of the solid compound 22 in a glass tube, some glass beads were added and the solid was milled by vortexing for 2 minutes. After addition of 1 ml of a solution of 1% methylcellulose and 5% mannitol in water, the compound was suspended by vortexing for 10 minutes. Finally the pH was adjusted to 7.

Example 4

Pharmacological Test Results

Dopamine-$D_2$ and serotonin reuptake receptor affinity data obtained according to the protocols given above are shown in the table below.

TABLE 2

In vitro affinities of compounds of the invention

| | In vitro affinity | |
|---|---|---|
| cpnd | Dopamine-$D_2$ pKi | 5-HT reuptake pKi |
| 1 | 7.7 | 8.8 |
| 7 | 7.8 | 9.5 |
| 10 | 7.8 | 8.8 |
| 11 | 8.0 | 8.6 |
| 14 | 7.0 | 7.3 |
| 15 | 8.1 | 8.4 |
| 18 | 7.5 | 9.1 |
| 19 | 8.2 | 7.6 |
| 20 | 7.0 | 8.1 |
| 21 | 7.5 | 9.8 |
| 22 | 8.1 | 8.8 |
| 24 | 8.0 | 8.1 |
| 27 | 7.2 | 9.5 |
| 33 | 7.3 | 8.5 |

The invention claimed is:

1. A tetrahydropyridin-4-yl indole compound of the formula (I), or a tautomer, a stereoisomer, an N-oxide, a salt, or a hydrate thereof:

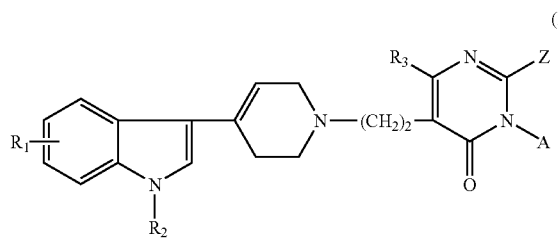

wherein:
$R_1$ is chosen from hydrogen, halogen, $(C_{1-3})$-alkyl, $(C_{1-3})$-alkoxy, CN and $CF_3$;
$R_2$ is chosen from hydrogen and $(C_{1-3})$-alkyl;
$R_3$ is chosen from hydrogen and $(C_{1-3})$-alkyl;
Z is chosen from hydrogen, $(C_{1-3})$-alkyl, $(C_{1-3})$-alkoxy and $(C_{1-3})$-alkylthio; and
A is chosen from hydrogen and $(C_{1-3})$-alkyl; or
Z and A together form a saturated, partly unsaturated, or unsaturated 5- or 6-membered ring optionally substituted with a substituent chosen from halogen, $(C_{1-3})$-alkyl and phenyl, wherein Z is chosen from carbon, sulfur and nitrogen.

2. The compound according to claim 1, or a tautomer, a stereoisomer, an N-oxide, a salt, or a hydrate thereof, wherein:
$R_1$ is chosen from hydrogen and halogen;
$R_2$ is hydrogen;
$R_3$ is $CH_3$;
Z is $SCH_3$; and
A is $CH_3$; or
Z and A together form a partly unsaturated or unsaturated 6-membered ring optionally substituted with a substituent chosen from $CH_3$, $C_2H_5$ and iso-$C_3H_7$.

3. The compound according to claim 1, or a tautomer, a stereoisomer, an N-oxide, a salt, or a hydrate thereof, wherein:
$R_1$ is hydrogen;
$R_2$ is hydrogen;
$R_3$ is $CH_3$; and
Z and A together represent —C($CH_3$)=CH—CH=CH—.

4. The compound according to claim 1, or a tautomer, a stereoisomer, an N-oxide, a salt, or a hydrate thereof, wherein the substituents of formula (I) are chosen from a combination of substituents $R_1$, $R_2$, $R_3$, Z and A chosen from: $R_1$ is H, $R_2$ is H, $R_3$ is $CH_3$ and Z+A is —CH=CH—CH=CH—; $R_1$ is 7-Cl, $R_2$ is H, $R_3$ is $CH_3$ and Z+A is —CH=CH—CH=OH—; $R_1$ is 5-$CH_3$, $R_2$ is H, $R_3$ is $CH_3$ and X+A is —CH=CH—CH=CH—; $R_1$ is 6-Cl, $R_2$ is H, $R_3$ is $CH_3$ and Z+A is —CH=CH—CH=CH—; $R_1$ is 5-Cl, $R_2$ is H, $R_3$ is $CH_3$ and Z+A is —CH=CH—CH=CH—; $R_1$ is 5-CN, $R_2$ is H, $R_3$ is $CH_3$ and Z+A is —CH=CH—CH=CH—; $R_1$ is 5-F, $R_2$ is H, $R_3$ is $CH_3$ and Z+A is —CH=CH—CH=CH—; $R_1$ is 5-Br, $R_2$ is H, $R_3$ is $CH_3$ and Z+A is —CH=CH—CH=CH—; $R_1$ is H, $R_2$ is H, $R_3$ is $CH_3$ and Z+A is —CH=CH—C($CH_3$)=CH—; $R_1$ is H, $R_2$ is H, $R_3$ is $CH_3$ and Z+A is —S—$CH_2$—$CH_2$—; $R_1$ is H, $R_2$ is H, $R_3$ is $CH_3$ and Z+A is —S—CH=CH—; $R_1$ is H, $R_2$ is H, $R_3$ is $CH_3$, Z is $SCH_3$ and A is $CH_3$; $R_1$ is 7-$CH_3$, $R_2$ is H, $R_3$ is $CH_3$ and Z+A is —CH=CH—CH=CH—; $R_1$ is H, $R_2$ is H, $R_3$ is $CH_3$, Z is $SCH_3$ and A is H; $R_1$ is H, $R_2$ is H, $R_3$ is $CH_3$, Z+A is —CH=C($CH_3$)—CH=CH—; $R_1$ is H, $R_2$ is H, $R_3$ is $CH_3$, Z+A is —S—CH=C($C_6H_5$)—; $R_1$ is H, $R_2$ is H, $R_3$ is $CH_3$ and Z+A is —NH—$(CH_2)_3$—; $R_1$ is H, $R_2$ is H, $R_3$ is $CH_3$, Z is $OCH_3$ and A is $CH_3$; $R_1$ is 5-F, $R_2$ is H, $R_3$ is $CH_3$, Z is $SCH_3$, and A is $CH_3$; $R_1$ is H, $R_2$ is $CH_3$, $R_3$ is $SCH_3$ and A is $CH_3$; $R_1$ is 5-F, $R_2$ is H, $R_3$ is $CH_3$ and Z+A is —CH=C($CH_3$)—CH=CH—; $R_1$ is H, $R_2$ is H, $R_3$ is $CH_3$ and Z+A is —C($CH_3$)=CH—CH=CH—; $R_1$ is H, $R_2$ is H, $R_3$ is $CH_3$ and Z+A is —CH=CH—CH=C($CH_3$)—; $R_1$ is 5-F, $R_2$ is H, $R_3$ is $CH_3$ and Z+A is —CH=C($C_2H_5$)—CH=CH—; $R_1$ is H, $R_2$ is H, $R_3$ is $CH_3$ and Z+A is —CH=C($C_2H_5$)—CH=CH—; $R_1$ is 5-F, $R_2$ is H, $R_3$ is $CH_3$ and Z+A is —C($CH_3$)=CH—CH=CH—; $R_1$ is H, $R_2$ is H, $R_3$ is $CH_3$ and Z+A is —CH=C($C_6H_5$)—CH=CH—; $R_1$ is 5-F, $R_2$ is H, $R_3$ is $CH_3$ and Z+A is —CH=C(i-$C_3H_7$)—CH=CH—; $R_1$ is H, $R_2$ is H, $R_3$ is $CH_3$ and Z+A is —CH=C(i-$C_3H_7$)—CH=CH—; $R_1$ is 5-Cl, $R_2$ is H, $R_3$ is $C_2H_5$, Z is H and A is $CH_3$; $R_1$ is 5-Br, $R_2$ is H, $R_3$ is $C_2H_5$, Z is H and A is $CH_3$; $R_1$ is 5-CN, $R_2$ is H, $R_3$ is $C_2H_5$, Z is, H and A is $CH_3$; and $R_1$ is 5-F, $R_2$ is H, $R_3$ is $CH_3$, Z is H and A is $CH_3$.

5. A method for preparing a compound of formula (I), or a tautomer, a stereoisomer, an N-oxide, a salt, or a hydrate thereof:

(I)

wherein a compound of formula (II)

(II)

is reacted under basic conditions with a compound of formula (III)

(III)

wherein:
- $R_1$ is chosen from hydrogen, halogen, $(C_{1-3})$-alkyl, $(C_{1-3})$-alkoxy, CN and $CF_3$;
- $R_2$ is chosen from hydrogen and $(C_{1-3})$-alkyl;
- $R_3$ is chosen from hydrogen and $(C_{1-3})$-alkyl;
- Z is chosen from hydrogen, $(C_{1-3})$-alkyl, $(C_{1-3})$-alkoxy and $(C_{1-3})$-alkylthio;
- A is chosen from hydrogen and $(C_{1-3})$-alkyl; or
- Z and A together form a saturated, partly unsaturated, or unsaturated 5- or 6-membered ring optionally substituted with a substituent chosen from halogen, $(C_{1-3})$-alkyl and phenyl, wherein Z is chosen from carbon, sulfur and nitrogen; and
- L is a leaving group.

6. A pharmaceutical composition comprising:
a pharmacologically active amount of at least one compound of formula (I), at least one tautomer thereof, at least one stereoisomer thereof, at least one N-oxide thereof, at least one salt thereof, at least one hydrate thereof-or a mixture of any two or more of the foregoing:

(I)

wherein:
- $R_1$ is chosen from hydrogen, halogen, $(C_{1-3})$-alkyl, $(C_{1-3})$-alkoxy, CN and $CF_3$;
- $R_2$ is chosen from hydrogen and $(C_{1-3})$-alkyl;
- $R_3$ is chosen from hydrogen and $(C_{1-3})$-alkyl;
- Z is chosen from hydrogen, $(C_{1-3})$-alkyl, $(C_{1-3})$-alkoxy and $(C_{1-3})$-alkylthio; and
- A is chosen from hydrogen and $(C_{1-3})$-alkyl; or
- Z and A together form a saturated, partly unsaturated, or unsaturated 5- or 6-membered ring optionally substituted with a substituent chosen from halogen, $(C_{1-3})$-alkyl and phenyl, wherein Z is chosen from carbon, sulfur and nitrogen; and
at least one pharmaceutically acceptable carrier, at least one pharmaceutically acceptable auxiliary substance, or a combination thereof.

7. The pharmaceutical composition according to claim 6, wherein, in formula (I):
- $R_1$ is chosen from hydrogen and halogen;
- $R_2$ is hydrogen;
- $R_3$ is $CH_3$;
- Z is $SCH_3$; and
- A is $CH_3$; or
- Z and A together form a partly unsaturated or unsaturated 6-membered ring optionally substituted with a substituent chosen from $CH_3$, $C_2H_5$ and iso-$C_3H_7$.

8. The pharmaceutical composition according to claim 7, wherein, in formula (I):
- $R_1$ is hydrogen;
- $R_2$ is hydrogen;
- $R_3$ is $CH_3$; and
- Z and A together represent —C($CH_3$)=CH—CH=CH—.

9. The pharmaceutical composition according to claim 7, wherein the substituents of formula (I) are chosen from a combination of substituents $R_1$, $R_2$, $R_3$, Z and A chosen from: $R_1$ is H, $R_2$ is H, $R_3$ is $CH_3$ and Z+A is —CH=CH—CH=CH—; $R_1$ is 7-Cl, $R_2$ is H, $R_3$ is $CH_3$ and Z+A is —CH=CH—CH=OH—; $R_1$ is 5-$CH_3$, $R_2$ is H, $R_3$ is $CH_3$ and X+A is —CH=CH—CH=CH—; $R_1$ is 6-Cl, $R_2$ is H, $R_3$ is $CH_3$ and Z+A is —CH=CH—CH=CH—; $R_1$ is 5-Cl, $R_2$ is H, $R_3$ is $CH_3$ and Z+A is —CH=CH—CH=CH—; $R_1$ is 5-CN, $R_2$ is H, $R_3$ is $CH_3$ and Z+A is —CH=CH—CH=CH—; $R_1$ is 5-F, $R_2$ is H, $R_3$ is $CH_3$ and Z+A is —CH=CH—CH=CH—; $R_1$ is 5-Br, $R_2$ is H, $R_3$ is $CH_3$ and Z+A is —CH=CH—CH=CH—; $R_1$ is H, $R_2$ is H, $R_3$ is $CH_3$ and Z+A is —CH=CH—C($CH_3$)=CH—; $R_1$ is H, $R_2$ is H, $R_3$ is $CH_3$ and Z+A is —S—$CH_2$—$CH_2$—; $R_1$ is H, $R_2$ is H, $R_3$ is $CH_3$ and Z+A is —S—CH=CH—; $R_1$ is H, $R_2$ is H, $R_3$ is $CH_3$, Z is $SCH_3$ and A is $CH_3$; $R_1$ is 7-$CH_3$, $R_2$ is H, $R_3$ is $CH_3$ and Z+A is —CH=CH—CH=CH—; $R_1$ is H, $R_2$ is H, $R_3$ is $CH_3$, Z is $SCH_3$ and A is H; $R_1$ is H, $R_2$ is H, $R_3$ is $CH_3$, Z+A is —CH=C($CH_3$)—CH=CH—; $R_1$ is H, $R_2$ is H, $R_3$ is $CH_3$, Z+A is —S—CH=C($C_6H_5$)—; $R_1$ is H, $R_2$ is H, $R_3$ is $CH_3$ and Z+A is —NH—$(CH_2)_3$—; $R_1$ is H, $R_2$ is H, $R_3$ is $CH_3$, Z is $OCH_3$ and A is $CH_3$; $R_1$ is 5-F, $R_2$ is H, $R_3$ is $CH_3$, Z is $SCH_3$, and A is $CH_3$; $R_1$ is H, $R_2$ is $CH_3$, $R_3$ is $SCH_3$ and A is $CH_3$; $R_1$ is 5-F, $R_2$ is H, $R_3$ is $CH_3$ and Z+A is —CH=C($CH_3$)—CH=CH—; $R_1$ is H, $R_2$ is H, $R_3$ is $CH_3$ and Z+A is —C($CH_3$)=CH—CH=CH—; $R_1$ is H, $R_2$ is H, $R_3$ is $CH_3$ and Z+A is —CH=CH—CH=C($CH_3$)—; $R_1$ is 5-F, $R_2$ is H, $R_3$ is $CH_3$ and Z+A is —CH=C($C_2H_5$)—CH=CH—; $R_1$ is H, $R_2$ is H, $R_3$ is $CH_3$ and Z+A is —CH=C($C_2H_5$)—CH=CH—; $R_1$ is 5-F, $R_2$ is H, $R_3$ is $CH_3$ and Z+A is —C($CH_3$)=CH—CH=CH—; $R_1$ is H, $R_2$ is H, $R_3$ is $CH_3$ and Z+A is —CH=C($C_6H_5$)—CH=CH—; $R_1$ is 5-F, $R_2$ is H, $R_3$ is $CH_3$ and Z+A is —CH=C(i-$C_3H_7$)—CH=CH—; $R_1$ is H, $R_2$ is H, $R_3$ is $CH_3$ and Z+A is —CH=C(i-$C_3H_7$)—CH=CH—; $R_1$ is 5-Cl, $R_2$ is H, $R_3$ is $C_2H_5$, Z is H and A is $CH_3$; $R_1$ is 5-Br, $R_2$ is H, $R_3$ is $C_2H_5$, Z is H and A is $CH_3$; $R_1$ is 5-CN, $R_2$ is H, $R_3$ is $C_2H_5$, Z is, H and A is $CH_3$; and $R_1$ is 5-F, $R_2$ is H, $R_3$ is $CH_3$, Z is H and A is $CH_3$.

10. A method for preparing a medicament, comprising combining an effective amount of at least one compound of formula (I), at least one tautomer thereof, at least one stereoisomer thereof, at least one N-oxide thereof, at least one salt thereof, or at least one hydrate thereof, or a mixture of any two or more of the foregoing, with at least one pharmaceutically acceptable carrier, at least one pharmaceutically acceptable auxiliary substance, or a combination thereof:

(I)

wherein:
$R_1$ is chosen from hydrogen, halogen, $(C_{1-3})$-alkyl, $(C_{1-3})$-alkoxy, CN and $CF_3$;
$R_2$ is chosen from hydrogen and $(C_{1-3})$-alkyl;
$R_3$ is chosen from hydrogen and $(C_{1-3})$-alkyl;
Z is chosen from hydrogen, $(C_{1-3})$-alkyl, $(C_{1-3})$-alkoxy and $(C_{1-3})$-alkylthio; and
A is chosen from hydrogen and $(C_1$-3)-alkyl; or
Z and A together form a saturated, partly unsaturated, or unsaturated 5- or 6-membered ring optionally substituted with a substituent chosen from halogen, $(C_{1-3})$-alkyl and phenyl, wherein Z is chosen from carbon, sulfur and nitrogen;
wherein the at least one compound of formula (I), at least one tautomer thereof, at least one stereoisomer thereof, at least one N-oxide thereof, at least one salt thereof, or at least one hydrate thereof or a mixture of any two or more of the foregoing.

11. A method for preparing a pharmaceutical composition comprising:
combining an effective amount of at least one compound of formula (I), at least one tautomer thereof, at least one stereoisomer thereof, at least one N-oxide thereof, at least one salt thereof, or at least one hydrate thereof, or a mixture of any two or more of the foregoing, with at least one pharmaceutically acceptable carrier, at least one pharmaceutically acceptable auxiliary substance, or a combination thereof:

(I)

wherein:
$R_1$ is chosen from hydrogen, halogen, $(C_{1-3})$-alkyl, $(C_{1-3})$-alkoxy, CN and $CF_3$;
$R_2$ is chosen from hydrogen and $(C_{1-3})$-alkyl;
$R_3$ is chosen from hydrogen and $(C_{1-3})$-alkyl;
Z is chosen from hydrogen, $(C_{1-3})$-alkyl, $(C_{1-3})$-alkoxy and $(C_{1-3})$-alkylthio; and
A is chosen from hydrogen and $(C_{1-3})$-alkyl; or
Z and A together form a saturated, partly unsaturated, or unsaturated 5- or 6-membered ring optionally substituted with a substituent chosen from halogen, $(C_{1-3})$-alkyl and phenyl, wherein Z is chosen from carbon, sulfur and nitrogen;
wherein the at least one compound of formula (I), at least one tautomer thereof, at least one stereoisomer thereof, at least one N-oxide thereof, at least one salt thereof, or at least one hydrate thereof, or a mixture of any two or more of the foregoing.

12. The method according to claim 11, wherein, in formula (I):
$R_1$ is chosen from hydrogen and halogen;
$R_2$ is hydrogen;
$R_3$ is $CH_3$;
Z is $SCH_3$; and
A is $CH_3$; or
Z and A together form a partly unsaturated or unsaturated 6-membered ring optionally substituted with a substituent chosen from $CH_3$, $C_2H_5$ and iso-$C_3H_7$.

13. The method according to claim 11, wherein, in formula (I):
$R_1$ is hydrogen;
$R_2$ is hydrogen;
$R_3$ is $CH_3$; and
Z and A together represent —C($CH_3$)=CH—CH=CH—.

14. The method according to claim 11, wherein the substituents of formula (I) are chosen from a combination of substituents $R_1$, $R_2$, $R_3$, Z and A chosen from: $R_1$ is H, $R_2$ is H, $R_3$ is $CH_3$ and Z+A is —CH=CH—CH=CH—; $R_1$ is 7-Cl, $R_2$ is H, $R_3$ is $CH_3$ and Z+A is —CH=CH—CH=OH—; $R_1$ is 5-$CH_3$, $R_2$ is H, $R_3$ is $CH_3$ and X+A is —CH=CH—CH=CH—; $R_1$ is 6-Cl, $R_2$ is H, $R_3$ is $CH_3$ and Z+A is —CH=CH—CH=CH—; $R_1$ is 5-Cl, $R_2$ is H, $R_3$ is $CH_3$ and Z+A is —CH=CH—CH=CH—; $R_1$ is 5-CN, $R_2$ is H, $R_3$ is $CH_3$ and Z+A is —CH=CH—CH=CH—; $R_1$ is 5-F, $R_2$ is H, $R_3$ is $CH_3$ and Z+A is —CH=CH—CH=CH—; $R_1$ is 5-Br, $R_2$ is H, $R_3$ is $CH_3$ and Z+A is —CH=CH—CH=CH—; $R_1$ is H, $R_2$ is H, $R_3$ is $CH_3$ and Z+A is —CH=CH—C($CH_3$)=CH—; $R_1$ is H, $R_2$ is H, $R_3$ is $CH_3$ and Z+A is —S—$CH_2$—$CH_2$—; $R_1$ is H, $R_2$ is H, $R_3$ is $CH_3$ and Z+A is —S—CH=CH—; $R_1$ is H, $R_2$ is H, $R_3$ is $CH_3$, Z is $SCH_3$ and A is $CH_3$; $R_1$ is 7-$CH_3$, $R_2$ is H, $R_3$ is $CH_3$ and Z+A is —CH=CH—CH=CH—; $R_1$ is H, $R_2$ is H, $R_3$ is $CH_3$, Z is $SCH_3$ and A is H; $R_1$ is H, $R_2$ is H, $R_3$ is $CH_3$, Z+A is —CH=C($CH_3$)—CH=CH—; $R_1$ is H, $R_2$ is H, $R_3$ is $CH_3$, Z+A is —S—CH=C($C_6H_5$)—; $R_1$ is H, $R_2$ is H, $R_3$ is $CH_3$ and Z+A is —NH—($CH_2$)$_3$—; $R_1$ is H, $R_2$ is H, $R_3$ is $CH_3$, Z is $OCH_3$ and A is $CH_3$; $R_1$ is 5-F, $R_2$ is H, $R_3$ is $CH_3$, Z is $SCH_3$, and A is $CH_3$; $R_1$ is H, $R_2$ is $CH_3$, $R_3$ is $SCH_3$ and A is $CH_3$; $R_1$ is 5-F, $R_2$ is H, $R_3$ is $CH_3$ and Z+A is —CH=C($CH_3$)—CH=CH—; $R_1$ is H, $R_2$ is H, $R_3$ is $CH_3$ and Z+A is —C($CH_3$)=CH—CH=CH—; $R_1$ is H, $R_2$ is H, $R_3$ is $CH_3$ and Z+A is —CH=CH—CH=C($CH_3$)—; $R_1$ is 5-F, $R_2$ is H, $R_3$ is $CH_3$ and Z+A is —CH=C($C_2H_5$)—CH=CH—; $R_1$ is H, $R_2$ is H, $R_3$ is $CH_3$ and Z+A is —CH=C($C_2H_5$)—CH=CH—; $R_1$ is 5-F, $R_2$ is H, $R_3$ is $CH_3$ and Z+A is —C($CH_3$)=CH—CH=CH—; $R_1$ is H, $R_2$ is H, $R_3$ is $CH_3$ and Z+A is —CH=C($C_6H_5$)—CH=CH—; $R_1$ is 5-F, $R_2$ is H, $R_3$ is $CH_3$ and Z+A is —CH=C(i-$C_3H_7$)—CH=CH—; $R_1$ is H, $R_2$ is H, $R_3$ is $CH_3$ and Z+A is —CH=C(i-$C_3H_7$)—CH=CH—; $R_1$ is 5-Cl, $R_2$ is H, $R_3$ is $C_2H_5$, Z is H and A is $CH_3$; $R_1$ is 5-Br, $R_2$ is H, $R_3$ is $C_2H_5$, Z is H and A is $CH_3$; $R_1$ is 5-CN, $R_2$ is H, $R_3$ is $C_2H_5$, Z is, H and A is $CH_3$; and $R_1$ is 5-F, $R_2$ is H, $R_3$ is $CH_3$, Z is H and A is $CH_3$.

15. A method of treating a CNS disorder in a patient in need thereof, comprising:

administering a pharmacologically effective amount of at least one compound of formula (I), at least one tautomer thereof, at least one stereoisomer thereof, at least one N-oxide thereof, at least one salt thereof, at least one hydrate thereof, or a mixture of any two or more of the foregoing:

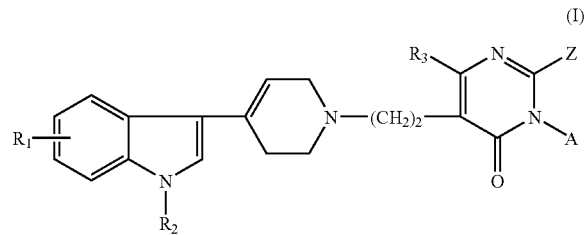

(I)

wherein:

$R_1$ is chosen from hydrogen, halogen, ($C_{1-3}$)-alkyl, ($C_{1-3}$)-alkoxy, CN and $CF_3$;

$R_2$ is chosen from hydrogen and ($C_{1-3}$)-alkyl;

$R_3$ is chosen from hydrogen and ($C_{1-3}$)-alkyl;

Z is chosen from hydrogen, ($C_{1-3}$)-alkyl, ($C_{1-3}$)-alkoxy and ($C_{1-3}$)-alkylthio; and A is chosen from hydrogen and ($C_{1-3}$)-alkyl; or Z and A together form a saturated, partly unsaturated, or unsaturated 5- or 6-membered ring optionally substituted with a substituent chosen from halogen, ($C_{1-3}$)-alkyl and phenyl, wherein Z is chosen from carbon, sulfur and nitrogen; and wherein the CNS disorder is chosen from vertigo, depression, Parkinsons' disease, and schizophrenia.

16. The method according to claim 15, wherein, in formula (I):

$R_1$ is chosen from hydrogen and halogen;

$R_2$ is hydrogen;

$R_3$ is $CH_3$;

Z is $SCH_3$; and

A is $CH_3$; or

A and Z together form a partly unsaturated or unsaturated 6-membered ring optionally substituted with a substituent chosen from $CH_3$, $C_2H_5$ and iso-$C_3H_7$.

17. The method according to claim 15, wherein, in formula (I):

$R_1$ is hydrogen;

$R_2$ is hydrogen;

$R_3$ is $CH_3$; and

Z and A together represent —C($CH_3$)=CH—CH=CH—.

18. The method according to claim 15, wherein the substituents of formula (I) are chosen from a combination of substituents $R_1$, $R_2$, $R_3$, Z and A chosen from: $R_1$ is H, $R_2$ is H, $R_3$ is $CH_3$ and Z+A is —CH=CH—CH=CH—; $R_1$ is 7-Cl, $R_2$ is H, $R_3$ is $CH_3$ and Z+A is —CH=CH—CH=OH—; $R_1$ is 5-$CH_3$, $R_2$ is H, $R_3$ is $CH_3$ and X+A is —CH=CH—CH=CH—; $R_1$ is 6-Cl, $R_2$ is H, $R_3$ is $CH_3$ and Z+A is —CH=CH—CH=CH—; $R_1$ is 5-Cl, $R_2$ is H, $R_3$ is $CH_3$ and Z+A is —CH=CH—CH=CH—; $R_1$ is 5-CN, $R_2$ is H, $R_3$ is $CH_3$ and Z+A is —CH=CH—CH=CH—; $R_1$ is 5-F, $R_2$ is H, $R_3$ is $CH_3$ and Z+A is —CH=CH—CH=CH—; $R_1$ is 5-Br, $R_2$ is H, $R_3$ is $CH_3$ and Z+A is —CH=CH—CH=CH—; $R_1$ is H, $R_2$ is H, $R_3$ is $CH_3$ and Z+A is —CH=CH—C($CH_3$)=CH—; $R_1$ is H, $R_2$ is H, $R_3$ is $CH_3$ and Z+A is —S—$CH_2$—$CH_2$—; $R_1$ is H, $R_2$ is H, $R_3$ is $CH_3$ and Z+A is —S—CH=CH—; $R_1$ is H, $R_2$ is H, $R_3$ is $CH_3$, Z is $SCH_3$ and A is $CH_3$; $R_1$ is 7-$CH_3$, $R_2$ is H, $R_3$ is $CH_3$ and Z+A is —CH=CH—CH=CH—; $R_1$ is H, $R_2$ is H, $R_3$ is $CH_3$, Z is $SCH_3$ and A is H; $R_1$ is H, $R_2$ is H, $R_3$ is $CH_3$, Z+A is —CH=C($CH_3$)—CH=CH—; $R_1$ is H, $R_2$ is H, $R_3$ is $CH_3$, Z+A is —S—CH=C($C_6H_5$)—; $R_1$ is H, $R_2$ is H, $R_3$ is $CH_3$ and Z+A is —NH—($CH_2$)$_3$—; $R_1$ is H, $R_2$ is H, $R_3$ is $CH_3$, Z is $OCH_3$ and A is $CH_3$; $R_1$ is 5-F, $R_2$ is H, $R_3$ is $CH_3$, Z is $SCH_3$, and A is $CH_3$; $R_1$ is H, $R_2$ is $CH_3$, $R_3$ is $SCH_3$ and A is $CH_3$; $R_1$ is 5-F, $R_2$ is H, $R_3$ is $CH_3$ and Z+A is —CH=C($CH_3$)—CH=CH—; $R_1$ is H, $R_2$ is H, $R_3$ is $CH_3$ and Z+A is —C($CH_3$)=CH—CH=CH—; $R_1$ is H, $R_2$ is H, $R_3$ is $CH_3$ and Z+A is —CH=CH—CH=C($CH_3$)—; $R_1$ is 5-F, $R_2$ is H, $R_3$ is $CH_3$ and Z+A is —CH=C($C_2H_5$)—CH=CH—; $R_1$ is H, $R_2$ is H, $R_3$ is $CH_3$ and Z+A is —CH=C($C_2H_5$)—CH=CH—; $R_1$ is 5-F, $R_2$ is H, $R_3$ is $CH_3$ and Z+A is —C($CH_3$)=CH—CH=CH—; $R_1$ is H, $R_2$ is H, $R_3$ is $CH_3$ and Z+A is —CH=C($C_6H_5$)—CH=CH—; $R_1$ is 5-F, $R_2$ is H, $R_3$ is $CH_3$ and Z+A is —CH=C(i-$C_3H_7$)—CH=CH—; $R_1$ is H, $R_2$ is H, $R_3$ is $CH_3$ and Z+A is —CH=C(i-$C_3H_7$)—CH=CH—; $R_1$ is 5-Cl, $R_2$ is H, $R_3$ is $C_2H_5$, Z is H and A is $CH_3$; $R_1$ is 5-Br, $R_2$ is H, $R_3$ is $C_2H_5$, Z is H and A is $CH_3$; $R_1$ is 5-CN, $R_2$ is H, $R_3$ is $C_2H_5$, Z is, H and A is $CH_3$; and $R_1$ is 5-F, $R_2$ is H, $R_3$ is $CH_3$, Z is H and A is $CH_3$.

* * * * *